United States Patent [19]

Willis et al.

[11] Patent Number: 4,510,319
[45] Date of Patent: Apr. 9, 1985

[54] FUNCTIONALIZATION OF TERMINAL TRISUBSTITUTED ALKENES AND DERIVATIVES THEREOF

[75] Inventors: Brian J. Willis, Ramsey, N.J.; Robert G. Eilerman, Merrick, N.Y.; Philip A. Christenson, Midland Park; John M. Yurecko, Jr., Bayonne, both of N.J.

[73] Assignee: Fritzsche Dodge & Olcott Inc., New York, N.Y.

[21] Appl. No.: 394,139

[22] Filed: Jul. 1, 1982

[51] Int. Cl.³ .................... C07C 69/02; C07C 67/02
[52] U.S. Cl. .................... 560/231; 252/522 R; 560/261; 560/262
[58] Field of Search .................... 560/231, 261, 262

[56] References Cited

U.S. PATENT DOCUMENTS

| | | | |
|---|---|---|---|
| 2,669,579 | 2/1954 | Urban | 560/262 |
| 3,679,756 | 7/1972 | Kretschmar et al. | 252/522 X |
| 4,387,047 | 6/1983 | Sundt et al. | 560/261 |

OTHER PUBLICATIONS

Bohlmann et al., Chem. Ber., vol. 107, 1773–1776, (1974).
Tschesche et al., Chem. Ber., vol. 110, 3111–3117, (1977).

Primary Examiner—Helen M. S. Sneed
Attorney, Agent, or Firm—Cooper, Dunham, Clark, Griffin & Moran

[57] ABSTRACT

The invention relates to a process for preparing compounds having the general structure:

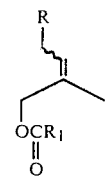

wherein R is hydrogen or an acyclic or alicyclic fragment containing between one and about ten carbon atoms, and $R_1$ is hydrogen or an alkyl containing between one and about four carbon atoms or an aryl group.

5 Claims, No Drawings

FUNCTIONALIZATION OF TERMINAL TRISUBSTITUTED ALKENES AND DERIVATIVES THEREOF

BACKGROUND OF THE INVENTION

New aroma chemicals and nature-identical synthetics which can be produced in an economical and straightforward manner are in demand by the fragrance industry. Such chemicals can be utilized in the duplication of fragrance notes associated with often costly natural materials, and for the creation of new fragrance effects.

The ability to introduce oxygen functionality at the terminal position of the isopropylidene group in terpenes with both regio- and stereochemical control provides access to a wide range of oxygenated terpenes of potential organoleptic value. Such chemicals may actually be present in essential oils or other natural products, or may already be known but not naturally occurring, or may be new. Present technology permits the preparation of some of these oxygenated terpene derivatives using reagents, such as selenium dioxide (see M. Fieser and L. Fieser, "Reagents for Organic Synthesis", Vol. 4, p. 423, Wiley-Interscience, 1974; and E. N. Trachtenberg "Oxidation Techniques and Applications in Organic Synthesis"; R. L. Augustine, Ed., Marcel Dekker, New York, N.Y., 1969, p. 119). However, the formation of malodorous organoselenium by-products can render these products organoleptically unacceptable for fragrance use.

Terpenes containing oxygen functionality at the terminal position of the isopropylidene group have been identified in nature. For example, (E)-2,6-dimethyl-2,7-octadien-1,6-diol having the structure:

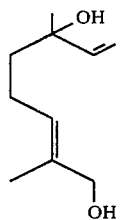

has been isolated from Greek tobacco by Behr et al., (see Acta Chem. Scand., 1978, B32, 228).

Also, (Z)-2-methyl-6-methylene-2,7-octadienol having the structure:

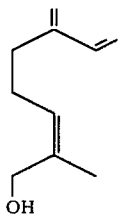

has been found by Granger et al., in the essential oil of certain species of *Thymus vulgaris* L. (see Phytochem., 1972, 11, 2301). The prior art gives no indication of the organoleptic properties of the above-mentioned chemicals and no prediction of the advantageous organoleptic properties of the novel compounds of this invention can be made.

Furthermore, East Indian sandalwood oil, a valuable essential oil, used in large quantities by the fragrance industry, contains the sesquiterpene alcohols, α-santalol having the structure:

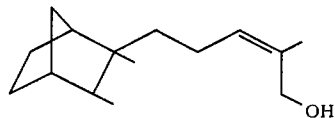

and β-santalol having the structure:

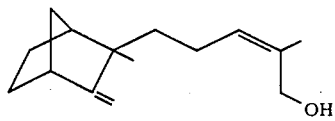

both of which are oxygenated at the terminal allylic position.

The santalols are generally considered to account for the main odor of East Indian sandalwood oil. Chemists have long sought syntheses of these compounds (see G. Bauchbauer, Chem. Ztg., 1977, 100, 225 and C. H. Heathcock in J. ApSimon "The Total Synthesis of Natural Products", Vol. 2 Wiley-Interscience, New York, 1973, pp. 481–491).

A major obstacle in the synthesis of α- and β-santalol is the stereoselective introduction of the Z-allylic alcohol functionality. Previous methods used to prepare the santalols have employed conditions or reagents that are difficult to adapt to an industrial scale, for example, air or moisture-sensitive reagents or low reaction temperatures were required (see, for example, E. J. Corey and H. Yamamoto, J. Amer. Chem. Soc., 1970, 92, 226), or such methods lead to predominantly the less desirable E-allylic alcohols as disclosed in U.S. Pat. No. 3,662,008. Also, U.S. Pat. Nos. 4,272,412 and 4,308,401 disclose a method for preparing halogen containing ionone derivatives by reacting a cyclohexanone derivative having the structure:

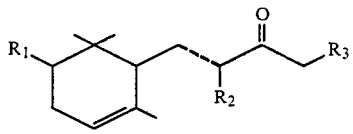

wherein the dashed line may be either a carbon-carbon single or double bond and $R_1$, $R_2$ and $R_3$ are each the same or different and each represent hydrogen or methyl, are reacted with a hypohalous acid to produce a chemical having the structure:

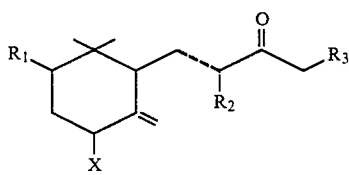

wherein X is a halogen. These chemicals were found to be useful as fragrance materials.

BRIEF DESCRIPTION OF THE INVENTION

This invention is concerned with a process for the preparation of an ester having the structure:

$$\underset{\underset{O}{\overset{\|}{OC-R_1}}}{\overset{R}{\diagup\kern-0.5em\diagdown}}$$

wherein R is hydrogen or an acyclic or alicyclic fragment containing between about one and about ten carbon atoms and $R_1$ is hydrogen or an alkyl having between about one and about four carbon atoms or an aryl group, which comprises:

(a) treating an isopropylidene derivative having the structure:

[structure with R]

with a hypohalous acid HOX wherein X is a halogen, to form an allylic halide having the structure:

[structure with R and X]

(b) reacting the allylic halide with the salt of a carboxylic acid having the structure:

$$\underset{O}{\overset{\|}{MOCR_1}},\ \underset{O}{\overset{\|}{M(OCR_1)_2}},\ \underset{O}{\overset{\|}{NH_4OCR_1}}$$

wherein M is a Group I or Group II metal, in the presence of a catalyst, to form an ester having the structure:

$$\underset{\underset{O}{\overset{\|}{OC-R_1}}}{\overset{R}{\diagup\kern-0.5em\diagdown}};$$

and (c) recovering said ester.

SUMMARY OF THE INVENTION

Broadly, the invention provides a method for the manufacture of both novel organic chemicals and known organic chemicals possessing valuable organoleptic properties useful in the manufacture of perfumes, perfume compositions, fine fragrances, as well as perfumed products such as soaps, detergents, deodorants, cosmetic preparations and the like. Importantly, the method permits variation in the stereoselective and regioselective course of the reaction by control of the reaction conditions. These chemicals are prepared according to the scheme:

[reaction scheme showing conversion with HO—X, then $MOCR_1$, $M(OCR_1)_2$ or $NH_4OCR_1$]

wherein the wavy line indicates a (Z)- and/or (E)-isomer and R is hydrogen or an acyclic or alicyclic fragment containing between about one and about ten carbon atoms, $R_1$ is hydrogen or an alkyl group having between about one and about four carbon atoms or an aryl group, M is a Group I or Group II metal and X is a halogen. By adjustment of the reaction conditions the stereochemistry of the final products may be controlled to provide isomeric mixtures in which either the (E)- or (Z)-isomer may predominate.

It will be recognized that the compounds of this invention can exist in different stereoisomeric forms. The structural formulae incorporated herein are intended to embrace the individual stereoisomers as well as mixtures of the various stereoisomers of the compounds of this invention.

The starting material utilized in carrying out the process of the present invention is a terminal isopropylidene derivative having the structure:

[structure I with R]

wherein R has the meaning set forth above. R may contain one or more alcohol, ether, ester, aldehyde, ketone, nitrile, double bond, or triple bond functional groups, or combinations of said functional groups.

Some specific examples of compounds falling within the scope of the foregoing structural formula include the following:

2-methyl-2-butene
2-methyl-2-pentene
2,4-dimethyl-2-pentene
6-methyl-5-hepten-2-one
2,6-dimethyl-5-hepten-2-ol
3,7-dimethyl-1,6-octadien-3-ol
3,7-dimethyl-6-octenol
3,7-dimethyl-1,6-octadien-3-yl formate
3,7-dimethyl-1,6-octadien-3-yl acetate
3,7-dimethyl-6-octen-1-yn-3-ol
3,7-dimethyl-2,6-octadienol
3,7-dimethyl-2,6-octadien-1-yl acetate
3,7-dimethyl-6-octenal
3,7-dimethyl-6-octene nitrile
3-methyl-3-methylene-1,6-octadiene
3,7-dimethyl-1,6-octadiene
3,7-dimethyl-2,6-octadienal
ethyl 3,7-dimethyl-2,6-octadienoate
6,10-dimethyl-3,5,9-undecatrien-2-one
6,10-dimethyl-5,9-undecadien-2-one
7,11-dimethyl-3-methylene-1,6,10-dodecatriene 3,7,11-trimethyl-1,3,6,10-dodecatetraene Some examples of alicyclic compounds falling within the scope of the foregoing structural formula include compounds having the structure:

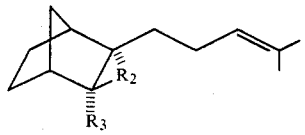

Ia

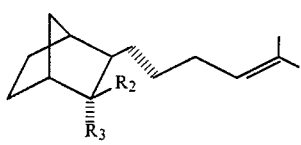

Ib and

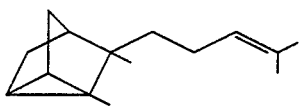

Ic wherein $R_2$ and $R_3$ can be either $=CH_2$, $=O$, and either OH or $CH_3$, $CH_2OH$ or H, $CO_2R_4$ (wherein $R_4=H$ or an alkyl containing between about 1 and about 4 carbon atoms) or H, and CN or H. Additional examples of alicyclic compounds include:

2-methyl-2-(4-methyl-3-pentenyl)-3-methylenebicyclo[2.2.1]heptane 3-methyl-3-(4-methyl-3-pentenyl)bicyclo[2.2.1]heptan-2-one 3-methyl-3-(4-methyl-3-pentenyl)bicyclo[2.2.1]heptane-2-carboxylic acid and its esters 1,7-dimethyl-7-(4-methyl-3-pentenyl)tricyclo[2.2.1.0$^{2,6}$]heptane 2,3-dimethyl-3-(4-methyl-3-pentenyl)bicyclo[2.2.1]heptan-2-ol 3-methyl-3-(4-methyl-3-pentenyl)bicyclo[2.2.1]heptane-2-methanol This listing of starting materials is not meant to be all inclusive, but merely gives some idea of the generality of the process.

In the first reaction step, the appropriate terminal isopropylidene derivative (I) is treated with a hypohalous acid (HOX) wherein X is a halogen, preferably chlorine or bromine, more preferably chlorine, in the presence of a suitable solvent such as dichloromethane, dichloroethane, diethyl ether, toluene or hexane. The hypohalous acid employed may be added directly to the reaction mixture, but it is most conveniently generated in situ from a salt, such as, for example, calcium hypochlorite by known methods (see H. O. House, "Modern Synthetic Reactions", W. A. Benjamin, Inc. 1972, p. 435). Reaction temperatures of between about −10° C. and about 50° C. can be employed with temperatures in the range of from about 5° C. to about 30° C. being preferred. Such treatment results in the formation of an allylic halide having the structure:

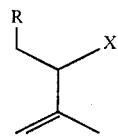

II

Reaction of the abovementioned alicyclic compounds Ia, Ib, and Ic provides novel halogen containing compounds having the structures:

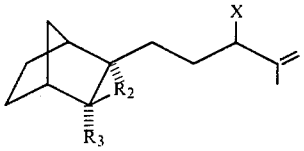

IIa

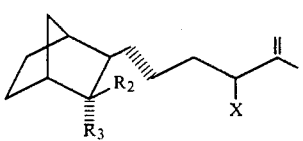

IIb and

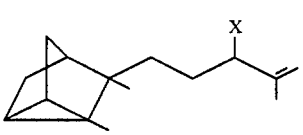

IIc wherein $R_1$ and $R_2$ can be either $=CH_2$, $=O$, and either OH or $CH_3$, $CH_2OH$ or H, $CO_2R_4$ (wherein $R_4$ is H or an alkyl containing between about 1 and about 4 carbon atoms) or H, and CN or H, and X is a halogen, preferably chlorine. Examples of novel halogen compounds falling within the scope of the foregoing structural formula include the following compounds:

2-endo-methyl-2-exo(3-chloro-4-methyl-4-pentenyl)-3-methylenebicyclo[2.2.1]heptane 2-exo-methyl-2-endo-(3-chloro-4-methyl-4-pentenyl)-3-methylbicyclo[2.2.1]heptane 3-(3-chloro-4-methyl-4-pentenyl)-2,3-endo-dimethylbicyclo[2.2.1]heptan-2-ol 3-exo-(3-chloro-4-methyl-4-pentenyl)-3-methylbicyclo[2.2.1]heptane-2-exo-carboxylic acid and its methyl and ethyl esters 3-exo-(3-chloro-4-methyl-4-pentenyl)-3-methylbicyclo[2.2.1]heptane-2-endo-carboxylic acid and its methyl and ethyl esters 3-(3-chloro-4-methyl-4-pentenyl)-3-endo-methylbicyclo[2.2.1]heptan-2-one 7-(3-chloro-4-methyl-4-pentenyl)-1,7-dimethyltricyclo[2.2.1.0$^{2,6}$]heptane Conversion of the allylic halide (II) to the ester compounds of the present invention may be accomplished by the methods outlined hereinafter. The allylic halide (II) is reacted with the salt of a carboxylic acid having the structure:

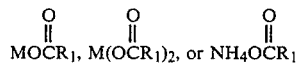

wherein M is a Group I or Group II metal and $R_1$ is as described hereinabove, in the presence of a catalyst, to form an ester having the structure:

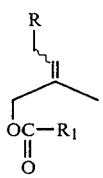

wherein R and R₁ are as described hereinabove.

The reaction is carried out in a suitable solvent, such as dimethylformamide, dimethylacetamide, toluene, xylene, hexamethylphosphoramide, N-methylpyrrolidone or acetonitrile. A wide variety of catalysts are suitable for use in the reaction. Suitable catalysts include Group I or Group II metal halides, Group II metal carboxylate salts, or quaternary ammonium halides. Temperatures in the range of between about 50° C. and about 180° C. and preferably between about 70° C. and 120° C. may be employed in the reaction. Reaction times of from about 1 to about 15 hours may be required depending upon the temperature and solvent utilized.

Generally, a mixture of (E)- and (Z)-isomers results from the reaction. However, by controlling the reaction temperature, mole ratio of the reactants, and the type and amount of catalyst, the stereochemical course of the reaction can be controlled to give a product predominating in either isomer.

Treatment of the allylic halide with a Group I or Group II metal carboxylate salt, preferably sodium formate or sodium acetate, using a mole ratio of allylic halide to carboxylate salt in the range of from about 1:1 to about 1:10 in the presence of a Group I or Group II metal halide or a quarternary ammonium halide, preferably where the halide is bromide or iodide, most preferably iodide, in an amount between about 1 mole percent and about 100 mole percent, preferably between about 1 and 10 mole percent, results in an ester which is predominantly the (Z)-isomer. Lower temperatures and lower mole percentages of the metal halide favor the formation of the (Z)-isomer. Conversely, higher temperatures and higher mole percentages of the metal halide favor the formation of the (E)-isomer.

Alternatively, a product containing predominantly the (E)-isomer may be prepared by reacting the allylic halide with a Group I or Group II metal carboxylate salt, preferably sodium formate, sodium acetate, potassium formate, or potassium acetate, in the presence of a copper (II) salt, preferably copper chloride or copper acetate. The reaction is carried out in a suitable solvent, such as dimethylformamide, dimethylacetamide, N-methylpyrrolidone, hexamethylphosphoramide, or propylene glycol. Temperatures in the range of about 50° C. to about 150° C. may be employed, with the temperature range of about 70° C. to about 120° C. being preferred. Reaction times of from about 1 to about 10 hours are required. The ratio of allylic halide to carboxylic acid salt may vary from about 1:1 to about 1:10 with the ratios from about 1:2 to about 1:4 being preferred. The amount of Copper II halide or carboxylate (based upon the allylic halide) may vary from about 5 to about 50 mole percent, the preferred amount being in the range about 10 to about 25 mole percent. The ester product obtained by the inventive process may be purified by conventional means, such as fractional distillation, or chromatography.

Various mixtures of the (Z) and (E)-stereoisomers of compounds III may be obtained by the process of this invention. These mixtures usually need not be separated into their components, since the organoleptic properties of both isomers are often similar.

The esters obtained by the process described hereinabove may be converted by hydrolysis to the corresponding alcohols having the structure:

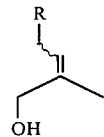

This may be accomplished by any one of the various conventional methods for the hydrolysis of esters (see J. March, "Advanced Organic Chemistry", McGraw-Hill, 1977 p. 349). For example, the ester may be hydrolyzed with an alkali metal hydroxide or carbonate in the presence of an aqueous alcoholic solvent system, such as methanol/water or ethanol/water.

In addition, compounds of this invention which contain both an ester and an alcohol group, such as, for example, the compound having the structure:

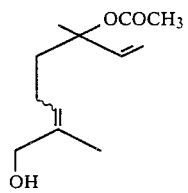

may be prepared from the corresponding diester having the structure:

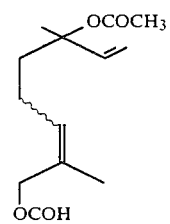

by conventional processes for selective hydrolysis. For example, the formate group may be selectively hydrolyzed in the presence of approximately one equivalent of a base such as an alkali metal hydroxide or carbonate, in a suitable solvent.

Specific examples of some compounds intended to be encompassed by the process of this invention together with a description of their olfactive properties are set forth in Table I below:

TABLE I

| NAME | STRUCTURE | ODOR EVALUATION |
|---|---|---|
| (Z)— and (E)—8-acetoxy-3,7-dimethyl-1,6-octadien-3-ol | 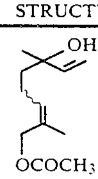 | green, tart sweet, floral fruity |

TABLE I-continued

| NAME | STRUCTURE | ODOR EVALUATION |
|---|---|---|
| (Z)— and (E)—3-acetoxy-8-hydroxy-3,7-dimethyl-1,6-octadiene | 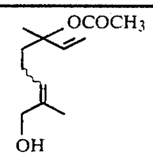 | tart, slightly acrid, floral |
| (Z)— and (E)—3-acetoxy-8-formyloxy-3,7-dimethyl-1,6-octadiene | 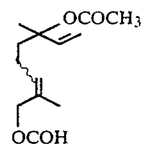 | low-keyed fruity, floral |
| (Z)— and (E)—3,8-diacetoxy-3,7-dimethyl-1,6-octadiene | 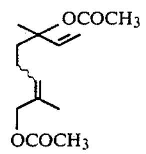 | floral, fruity (pineapple-like) |
| (Z)— and (E)—8-acetoxy-3,7-dimethyl-6-octene nitrile | 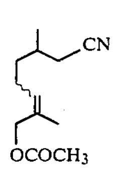 | low-keyed floral, fruity |
| (Z)— and (E)—8-hydroxy-3,7-dimethyl-6-octenal | 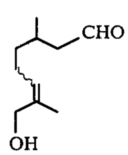 | woody, minty floral, similar to hydroxy citronellal |
| (9Z)— and (9E)—11-acetoxy-6,10-dimethyl-3,5,9-undecatrien-2-one | 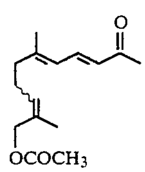 | long-lasting note (nerolidol, farnesol direction |
| (Z)— and (E)—8-acetoxy-3-methylene-1,6-octadiene | 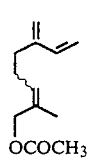 | tart, sweet, floral, fruity (apple) |
| (Z)— and (E)—8-acetoxy-3,7-dimethyl-1,6-octadiene | 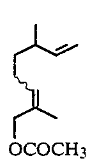 | tart, fresh fruity, floral |
| (6E,10Z)— and (6E,10E)—12-formyloxy-3-methylene-7,11-dimethyl-1,6,10-dodecatriene | 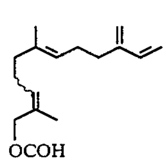 | long lasting, floral, fruity slightly woody character |

On the basis of their valuable olfactory properties, the inventive compounds or mixtures thereof have been found to be suitable for use in fine fragrance compositions as well as perfumed products, such as soaps, detergents, deodorants, cosmetic preparations and the like.

Such fragrance compositions comprise an organoleptically effective amount of the novel composition and at least one other organoleptic agent. One or more of the oxygenated derivatives of this invention and auxiliary perfume ingredients, for example, alcohols, aldehydes, ketones, nitriles, esters and essential oils, may be admixed so that the combined odors of the individual components produce a desired fragrance. Such perfume compositions are carefully balanced, harmonious blends of essential oils, aroma chemicals, resinoids and other extracts of natural odorous materials. Each ingredient imparts its own characteristic effect to the composition. Thus, one or more of the oxygenated derivatives of the invention can be employed to impart novel characteristics to fragrance compositions. The novel compositions provide a method for modifying, enhancing or improving the organoleptic properties of perfume compositions, colognes and perfumed articles by adding thereto an organoleptically effective amount of the novel chemicals of this invention.

The following examples are set forth herein to illustrate the preferred methods of synthesis of the compounds of this invention and their use in fragrance compositions. These examples are intended only to illustrate the preferred embodiments of this invention and are in no way meant to limit the scope thereof.

Unless otherwise stated, weights, temperatures and pressures are given in grams, degrees Centigrade and mm Hg., respectively. Where GLC percentages are indicated they refer to computer calculated peak areas without corrections for response.

EXAMPLE 1

Preparation of 3-Acetoxy-6-chloro-3,7-dimethyl-1,7-octadiene

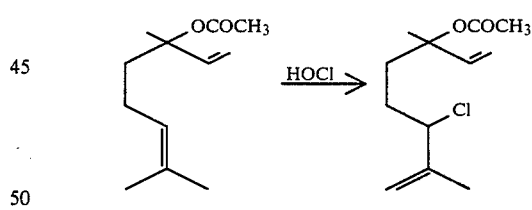

A stirred mixture of linalyl acetate (39 g, 0.2 mol), 65% calcium hypochlorite (22 g, 0.1 mol), water (70 mL) and dichloromethane (700 mL) was cooled to 10° C. and solid carbon dioxide was added until an exotherm was no longer observed upon addition. After stirring for an additional 1 h at 10° C., the organic layer was separated and washed successively with a solution containing 5% sodium bicarbonate and 1% sodium bisulfite (100 mL), and then with brine (100 mL). The organic layer was dried, the solvent evaporated, and the residue distilled to yield 41 g of 3-acetoxy-6-chloro-3,7-dimethyl-1,7-octadiene, bp 75°–80° C. (0.5 mm). IR (film) 1740, 1370, 1250, 920 cm$^{-1}$. NMR (CDCl$_3$) δ1.53 (3H, s), 1.8 (3H, bs), 1.8–2.4 (2H, m), 4.33 (1H, m), 4.84–5.33 (4H, complex) 6.0 (1H, dd).

EXAMPLE 2

Preparation of (Z)- and (E)-3-Acetoxy-8-formyloxy-3,7-dimethyl-1,6-octadiene

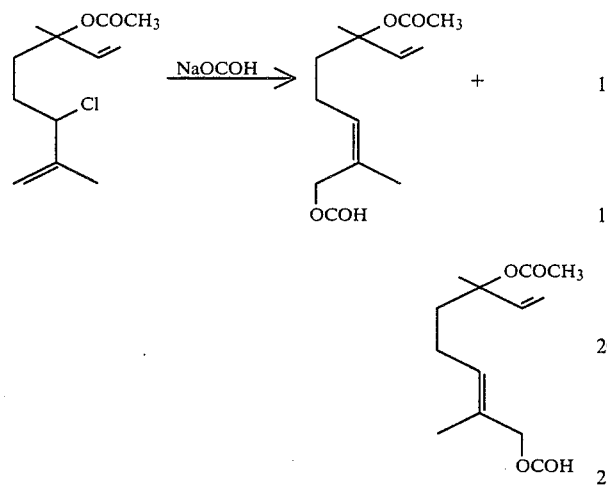

3-Acetoxy-6-chloro-3,7-dimethyl-1,7-octadiene (23.1 g, 0.1 mol), sodium formate (34.0 g, 0.5 mol) and potassium iodide (16.6 g, 0.1 mol) were combined in N,N-dimethylformamide (100 mL) and warmed to 100° C. with agitation. After 2 h, the mixture was cooled, poured into water and extracted with diethyl ether. The extract was washed with 5% sodium bicarbonate (100 mL) and brine (100 mL), and then dried. Evaporation of the solvent and distillation of the residue afforded 16 g of a mixture of (Z)-and (E)-3-acetoxy-8-formyloxy-3,7-dimethyl-1,6-octadiene (49% and 45%, respectively), bp 100°-102° C. (0.5 mm). The two isomers can be separated by preparative GLC. (Z)-isomer: IR (film) 1740, 1370, 1240, 1160 cm$^{-1}$. NMR (CDCl$_3$) δ 1.53 (3H, s), 1.77 (3H, s), 2.0 (3H, s), 1.7-2.3 (4H, complex), 4.67 (2H, s), 4.84-5.33 (2H, m), 5.43 (1H, m), 6.0 (1H, dd). MS (m/e) 43, 119, 41, 93. (E)-isomer: IR (film) 1740, 1370, 1240, 1160 cm$^{-1}$. NMR (CDCl$_3$) δ 1.53 (3H, s), 1.67 (3H, s), 2.0 (3H, s), 1.7-2.3 (4H, complex) 4.57 (2H, s), 4.84-5.33 (2H, m), 5.43 (1H, m), 6.0 (1H, dd). MS (m/e) 43, 119, 93, 41.

EXAMPLE 3

Preparation of (Z)- and (E)-3-Acetoxy-8-hydroxy-3,7-dimethyl-1,6-octadiene

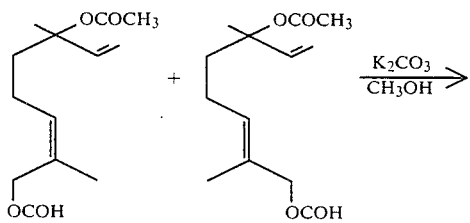

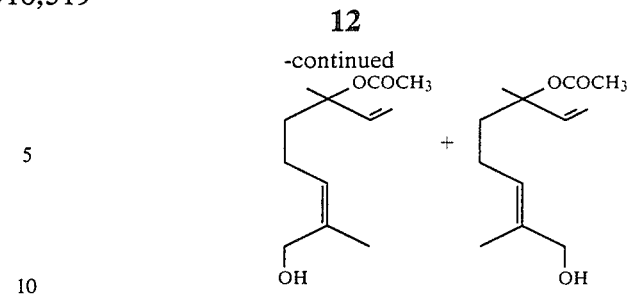

A mixture of (Z)- and (E)-3-acetoxy-8-formyloxy-3,7-dimethyl-1,6-octadiene (103 g, 0.43 mol), prepared by the procedure of Example 2, was added to potassium carbonate (37 g, 0.268 mol) in aqueous methanol (350 mL) and agitated at room temperature for 1 h. The reaction mixture was poured into water (500 mL) and extracted with diethyl ether. The organic layer was washed to neutrality, dried and the solvent evaporated. Distillation of the residue gave 45 g of a mixture of (Z)- and (E)-3-acetoxy-8-hydroxy-3,7-dimethyl-1,6-octadiene (53% and 34%, respectively), bp 105°-110° C. (1 mm). (Z)-isomer: IR (film) 3420, 1740, 1250 cm$^{-1}$. NMR (CDCl$_3$) δ 1.5 (3H, s), 1.77 (3H, s), 2.0 (3H, s), 4.07 (2H, s), 4.84-5.5 (3H, m), 5.93 (1H, dd), 2.4 (1H, bs). MS (m/e) 43, 67, 82, 41. (E)-isomer: IR (film) 3420, 1740, 1250 cm$^{-1}$. NMR (CDCl$_3$) δ 1.50 (3H, s), 1.63 (3H, s), 2.0 (3H, s), 3.93 (2H, s), 4.84-5.5 (3H, m), 5.93 (1H, dd), 2.4 (1H, bs). MS (m/e) 43, 67, 82, 41.

EXAMPLE 4

Preparation of (Z)- and (E)-8-Acetoxy-3,7-dimethyl-1,6-octadiene-3-ol

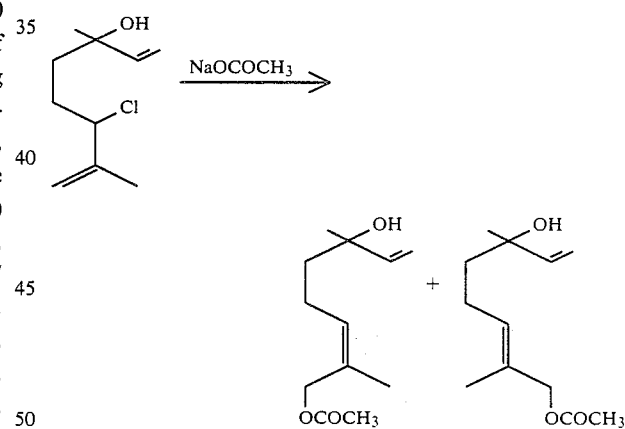

A mixture of 6-chloro-3,7-dimethyl-1,7-octadien-3-ol (18 g, 0.096 mol), prepared according to the method described in Example 1, sodium acetate (32.8 g 0.4 mol), and potassium iodide (5 g, 0.03 mol) in N,N-dimethylacetamide (150 mL) was stirred at 100° C. for 6 h. The mixture was cooled, poured into water and extracted with diethyl ether. The ether extract was washed with 5% sodium bicarbonate (100 mL) and brine (100 mL). The organic layer was dried, the solvent evaporated, and the residue distilled to yield 2.5 g of a mixture of (Z)- and (E)-8-acetoxy-3,7-dimethyl-1,6-octadiene-3-ol (60% and 29%, respectively), bp 98°-105° C. (0.5 mm). (Z)-isomer: IR (film) 3425, 1740, 1370, 1240, 1020 cm$^{-1}$. NMR (CDCl$_3$) δ 1.29 (3H, s), 1.73 (3H, s), 2.05 (3H, s), 1.6-2.3 (5H, complex), 4.60 (2H, s), 4.9-5.5 (3H, m), 5.93 (1H, dd). MS (m/e) 43, 119, 41, 45. (E)-isomer: IR (film) 3425, 1740, 1270, 1240, 1020 cm⁻¹. NMR (CDCl₃) δ 1.29 (3H, s), 1.66 (3H, s), 2.06 (3H, s), 1.6–2.3 (5H, complex), 4.43 (2H, s), 4.9–5.6 (3H, m), 5.93 (1H, dd). MS (m/e) 43, 119, 41, 45.

EXAMPLE 5

Preparation of (Z)- and (E)-3,8-Diacetoxy-3,7-dimethyl-1,6-octadiene and 3,6-Diacetoxy-3,7-dimethyl-1,7-octadiene

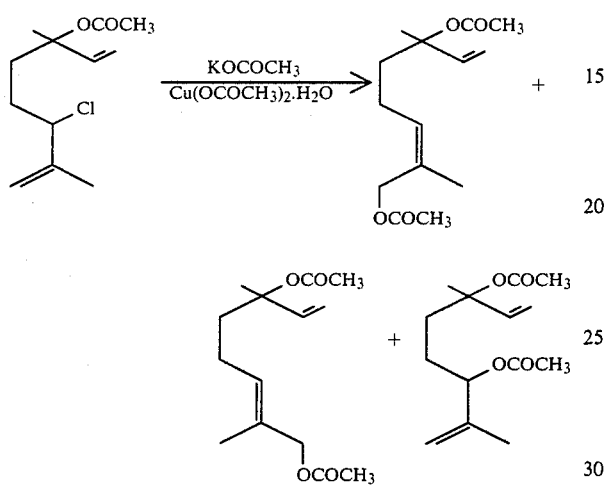

A mixture of 3-acetoxy-6-chloro-3,7-dimethyl-1,7-octadiene (11.5 g, 0.05 mol), prepared according to Example 1, potassium acetate (14.7 g, 0.15 mol), and copper (II) acetate monohydrate (2 g, 0.01 mol) in N,N-dimethylacetamide (50 mL) was stirred for 9 h at 100° C. The reaction mixture was poured into water and extracted with diethyl ether. The extracts were washed with 5% sodium bicarbonate (50 mL) and brine (50 mL). Evaporation of the solvent and distillation afforded 9.5 g of distillate as a mixture (GLC) of (E)-3,8-diacetoxy-3,7-dimethyl-1,6-octadiene (55%), (Z)-3,8-diacetoxy-3,7-dimethyl-1,6-octadiene (5%) and 3,6-diacetoxy-3,7-dimethyl-1,7-octadiene (34%). These isomers can be separated by preparative GLC. The (Z)- and (E)-mixture can be separated from the internal diacetoxy derivative by careful distillation. (Z)-isomer: IR (film) 1740, 1370, 1240, 1020 cm⁻¹. NMR (CDCl₃) δ 1.53 (3H, s), 1.77 (3H, s), 1.97 (3H, s), 2.03 (3H, s), 1.8–2.4 (4H, complex), 4.57 (2H, s), 5.0–5.67 (3H, m), 6.0 (1H, dd). MS (m/e) 43, 119, 41, 45. (E)-isomer: IR (film) 1740, 1370, 1240, 1020 cm⁻¹. NMR (CDCl₃) δ 1.53 (3H, s), 1.64 (3H, s), 1.97 (3H, s), 2.03 (3H, s), 1.8–2.4 (4H, complex), 4.43 (2H, s), 5.0–5.6 (3H, m), 6.0 (1H, dd). MS (m/e) 43, 119, 41, 45. Internal isomer: IR (film) 1740, 1370, 1240, 1020 cm⁻¹. NMR (CDCl₃) δ 1.64 (3H, s), 2.00 (3H, s), 2.03 (3H, s), 2.07 (3H, s), 1.8–2.4 (4H, m), 4.33 (1H, m), 4.83–5.50 (4H, m), 6.00 (1H, dd). MS (m/e) 43, 41, 119, 67.

EXAMPLE 6

Preparation of (Z)- and (E)-8-Acetoxy-3-methylene-1,6-octadiene

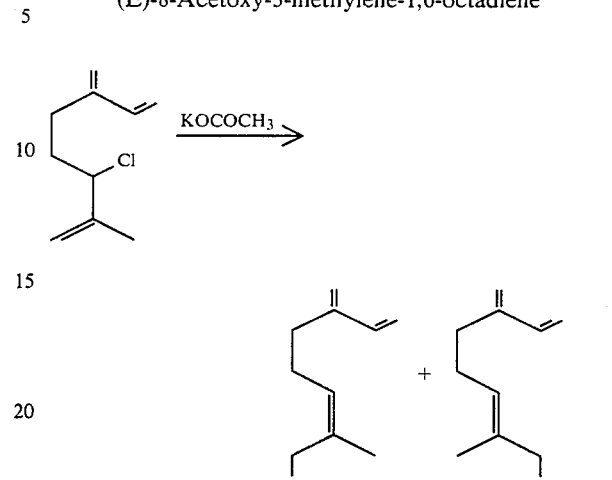

A mixture of 6-chloro-3-methylene-1,7-octadiene (225 g, 1.3 mol), prepared from myrcene according to the method described in Example 1, potassium acetate (254 g, 2.6 mol) and potassium iodide (32.4 g, 0.195 mol) in N,N-dimethylacetamide (975 mL) was stirred at 80° C. for 5 h. The mixture was poured into water and extracted with toluene. After washing, the solvent was evaporated and the residue distilled to yield 53 g of a mixture of (Z)- and (E)-8-acetoxy-3-methylene-1,6-octadiene (65% and 21%, respectively), bp 91°–95° C. (3 mm). (Z)-isomer: IR (film) 1740, 1220, 1020, 990 cm⁻¹. NMR (CDCl₃) δ 1.70 (3H, s), 2.03 (3H, s), 2.40 (4H, m), 4.53 (2H, s), 4.93–5.67 (5H, m), 6.33 (1H, dd). MS (m/e) 43, 93, 119, 134. (E)-isomer: IR (film) 1740, 1220, 990 cm⁻¹. NMR (CDCl₃) δ 1.53 (3H, s), 2.03 (3H, s), 2.4 (4H, m), 4.40 (3H, s), 4.93–5.76 (5H, m), 6.33 (1H, dd). MS (m/e) 43, 134, 119, 93.

EXAMPLE 7

Preparation of (Z)- and (E)-8-Hydroxy-3,7-dimethyl-6-octenal

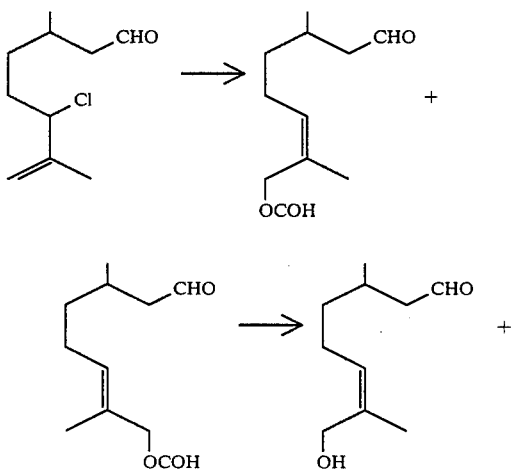

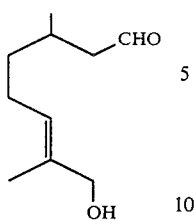

A mixture of 6-chloro-3,7-dimethyl-7-octenal (21 g, 0.12 mol), prepared according to the procedure outlined in Example 1, potassium iodide (4.2 g, 0.025 mol) and sodium formate (24.5 g, 0.36 mol) in N,N-dimethylacetamide (120 mL) was warmed to 75° C. After 5 h, the mixture was poured into water and extracted with diethyl ether. The ether extracts were washed with brine (150 mL) and dried. Evaporation of the solvent and distillation afforded 9.8 g of a mixture of (Z)- and (E)-8-formyloxy-3,7-dimethyl-6-octenal (60% and 31%, respectively), bp 88°-95° C. (0.5 mm). IR (film) 2710, 1730, 1165 cm⁻¹. NMR (CDCl₃) δ1.0 (3H, d), 1.73 (3H, 2s, (Z) and (E) olefinic methyl), 1.2-2.55 (7H, complex), 4.53 (s, (E) —CH₂OCOH), 4.67 (s, (Z) —CH₂OCOH), 5.40 (1H, m), 8.05 (1H, s) 9.83 (1H, bs). MS of major isomer (m/e) 93, 41, 43, 109.

This mixture of (Z)- and (E)-formates (6.0 g, 0.03 mol) was added to potassium carbonate (2.2 g, 0.016 mol) in methanol and agitated at 15° C. for 2 h. After dilution with water (150 mL), the product was isolated by extraction with diethyl ether. Distillation afforded 3.5 g of a mixture of (Z)- and (E)-8-hydroxy-3,7-dimethyl-6-octenal (55% and 30%, respectively), bp 105°-110° C. (0.5 mm). IR (film) 3400, 1725, 1005 cm⁻¹. NMR (CDCl₃) δ 1.0 (3H, bd), 1.25-2.6 (11H, complex pattern with bs at 1.65 and 1.76 for (E) and (Z) olefinic methyl groups), 4.0 (s, (E) —CH₂OH), 4.12 (s, (Z) —CH₂OH), 5.35 (1H, m), 9.7 1H, t). MS of major isomer (m/e) 93, 41, 43, 109.

EXAMPLE 8

Preparation of (6E,10Z)- and (6E,10E)-12-Formyloxy-3-methylene-7,11-dimethyl-1,6,10-dodecatriene

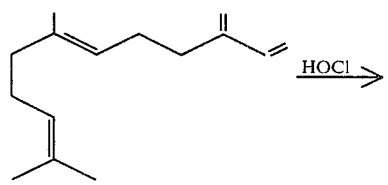

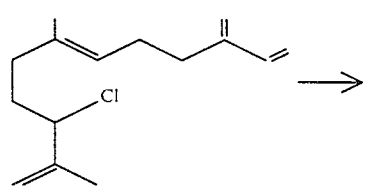

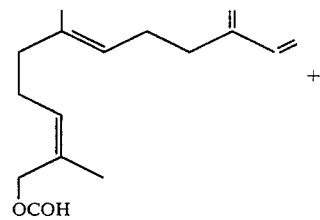

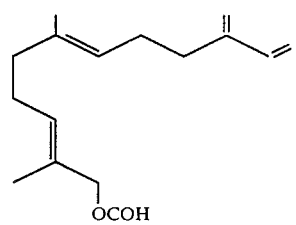

The allylic chloride from trans-β-farnesene was prepared according to Example 1. Treatment of the chloride (200 g, 0.83 mol) with sodium formate (190 g, 2.7 mol) and potassium iodide (139 g, 0.83 mol) in N,N-dimethylformamide (300 mL) at 90° C. for 1.5 h resulted in the isolation of 45 g of a mixture of the (6E,10Z)- and (6E,10E)-formates (3:2 ratio), bp 120°-130° C. (0.5 mm). IR (film) 1720, 1590, 1160, 890 cm⁻¹. NMR (CDCl₃) δ 1.2-1.8 (6H, m), 1.8-2.4 (8H, m), 4.53 (s, —CH₂OCOH, (E)-isomer), 4.67 (s, —CH₂OCOH, (Z)-isomer), 4.48-5.67 (6H, m) 6.34 (1H, dd) 8.07 (1H, s). MS of major isomer (m/e) 248 (M+), 93, 132, 41, 91.

EXAMPLE 9

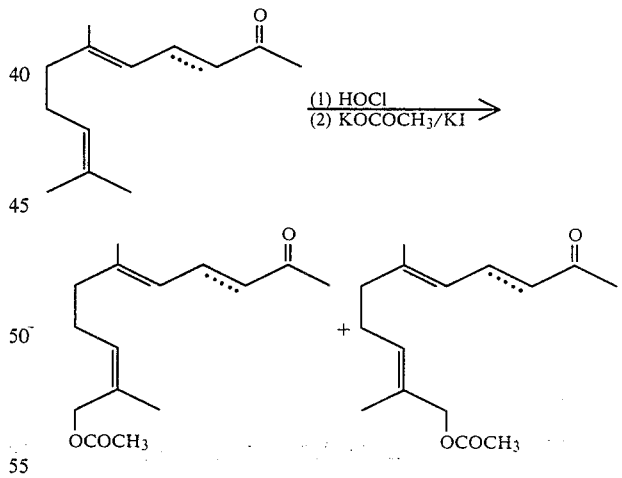

(9Z)- and (9E)-11-Acetoxy-6,10-dimethyl-3,5,9-undecatrien-2-one:

A mixture of the above isomers was obtained by a process similar to that resulting from a combination of Examples 1 and 4. In this fashion a 67% yield of a mixture of the (Z)- and (E)-isomers (57% and 25%, respectively), bp 145°-150° C. (0.5 mm), was obtained. IR (film) ν_max 1740, 1660, 1630, 1240 cm⁻¹. NMR (CDCl₃) δ 2.03 (3H, s), 2.23 (3H, s), 4.40 (2H, s), (E)- and (Z)-isomers. MS (m/e) 43, 109, 41, 81.

(9Z)- and (9E)-11-Acetoxy-6,10-dimethyl-5,9-undecadien-2-one may be prepared in a similar fashion.

EXAMPLE 10

Preparation of (Z)- and (E)-1-Acetoxy-2,5-dimethyl-1,7-octadiene

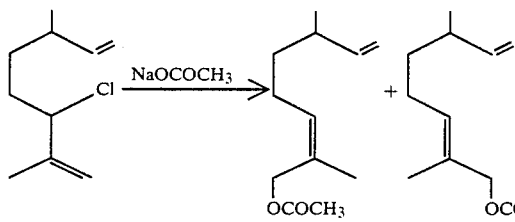

3-Chloro-2,6-dimethyl-1,7-octadiene (520 g, 3.06 mol) was added over a 1.5 h period at 90°-95° C. to a vigorously agitated mixture of sodium acetate (637, 6.55 mol), potassium iodide (18.8 g, 0.113 mol) and N,N-dimethylformamide 55 mL). After 5 h, the mixture was cooled, poured into water and extracted with hexane. The extract was washed successively with 1% sodium bisulfite (500 mL), 5% hydrochloric acid (1000 mL), water (500 mL), 5% sodium bicarbonate, and brine, followed by drying. Evaporation of the solvent and distillation of the residue afforded 393.3 g of a mixture of (Z)- and (E)-1-acetoxy-2,6-dimethyl-1,7-octadiene (58% and 27%, respectively), bp 99°-104.5° C. (10 mm). The two isomers can be separated by preparative GLC. (Z)-isomer: IR (film) $\nu_{max}$ 1740, 1260, 1020, 800 cm$^{-1}$. NMR (CDCl$_3$) $\delta$ 0.98 (3H, d), 1.30-1.28 (2H, m), 2.06 (3H, s), 2.1 (3H, m) 4.57 (2H, s), 4.90-4.99 (2H, m), 5.39 (1H, t), 5.41-5.67 (1H, m). MS (m/e) 43, 81, 97, 41. (E)-isomer: IR (film) $\nu_{max}$ 1740, 1220, 1020, 790 cm$^{-1}$. NMR (CDCl$_3$) $\delta$ 0.98 (3H, d), 1.34-1.57 (2H, m), 1.64 (3H, s), 2.07 (3H, s), 2.08 (3H, m), 4.45 (2H, s), 4.91-5.00 (2H, m), 5.45 (1H, t), 5.68 (1H, m). MS (m/e) 43, 81, 154, 79.

EXAMPLE 11

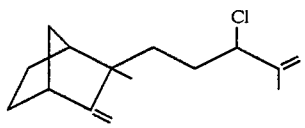

Solid carbon dioxide (0.5 g) was added to a mixture of 2-endo-methyl-2-exo-(4-methyl-3-pentenyl)-3-methylenebicyclo[2.2.1]heptene ($\beta$-santalene) (0.102 g), methylene chloride (3 mL), 65% calcium hypochlorite (0.055 g) and water (0.3 mL) at 25° C. over a 1 h period. Methylene chloride (10 mL) was added. The mixture was decanted from precipitated salts and washed with sodium bicarbonate solution. The solvent was evaporated to yield 0.117 g (98%) of 2-endo-methyl-2-exo-(3-chloro-4-methyl-4-pentenyl)-3-methylenebicyclo[2.2.1-]heptane. NMR (CDCl$_3$) $\delta$ 1.03 (3H, s), 1.0-2.4 (11H, m), 1.80 (3H, s), 2.7-2.9 (1H, m), 4.20-4.70 (1H, m), 4.50 and 4.76 (2H, s), 4.90 and 5.02 (2H, 2 broad s). IR (film) $\nu_{max}$ 2950, 1650, 1455, 895, 875 cm$^{-1}$.

EXAMPLE 12

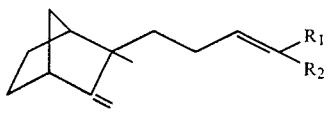

R$_1$, R$_2$=CH$_3$ or CH$_2$OAc

A mixture of 2-endo-methyl-2-exo-(3-chloro-4-methyl-4-pentenyl)-3-methylenebicyclo[2.2.1]heptane (0.117 g), potassium acetate (0.147 g), potassium iodide (0.017 g) and N,N-dimethylacetamide (1 mL) was heated at 90°-100° C. for 2 h. The mixture was cooled, poured into water and extracted with hexane. The extracts were washed sequentially with water and with sodium bicarbonate solution, and the solvent evaporated to give 0.099 g (77%) of (Z,E)-2-methyl-5-(2-endo-methyl-3-methylenebicyclo[2.2.1]hept-2-yl)-2-penten-1-ol acetates ($\beta$-santalol acetates). NMR analysis indicates that the Z/E ratio is 3:1. NMR (CDCl$_3$) $\delta$ 1.03 (3H, s), 1.63 and 1.72 (3H, 2 broad s, E/Z isomers, respectively), 1.0-1.90 (9H, m), 2.03 (3H, s), 1.9-2.9 (3H, m), 4.43 and 4.57 (2H, 2s, ratio; 1:3, —CH$_2$—OAc), 4.43 and 4.71 (2H, 2s), 5.1-5.5 (1H, m), IR (film) $\nu_{max}$ 2960, 1735, 1650, 875 cm$^{-1}$.

EXAMPLE 13

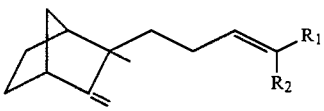

R$_1$, R$_2$=CH$_3$ or CH$_2$OH

A mixture of (Z,E)-2-methyl-5-(2-endo-methyl-3-methylenebicyclo[2.2.1]hept-2-yl)-2-penten-1-ol acetate (0.099 g), potassium hydroxide (0.1 g), methanol (5 mL) and water (1 mL) was heated at 60° C. for 5 min. and then stirred at 25° C. for 20 min. Water was added and the mixture extracted with hexane/ethyl acetate (4:1). Evaporation of solvents and kugelrohr distillation (130° C., 0.3 mm) of the residue gave 0.82 g (99% yield) of colorless oil which GLC analysis shows contains 78% of 2-methyl-5-(2-endo-methyl-3-methylenebicyclo[2.2.1]-hept-2-yl)-2-penten-1-ol ($\beta$-santalol) with Z/E ratio of 71:29. NMR (CDCl$_3$) $\delta$ 1.03 (3H, s), 1.62 and 1.73 (3H, 2 broad s, E/Z isomers), 1.0-1.90 (10H, m) 1.9-2.8 (3H, m), 3.93 and 4.08 (2H, 2s, E/Z ratio 7:3, —CH$_2$—OH), 4.43 and 4.70 (2H, 2s,), 5.1-5.5 (1H, m). IR (film) $\nu_{max}$ 3330, 2950, 1660, 875 cm$^{-1}$.

EXAMPLE 14

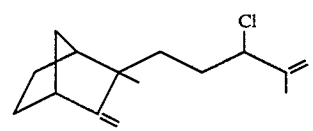

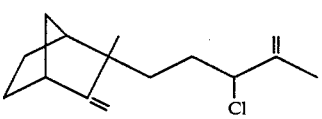

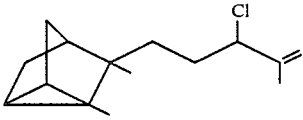

A mixture of santalenes (0.408 g, containing 43% of 7-(4-methyl-3-pentenyl)-1,7-dimethyltricyclo[2.2.1.0$^{2,6}$]-heptane, 23% of 3-endo-methyl-2-exo-(4-methyl-3-pentenyl)-3-methylenebicyclo[2.2.1]heptane and 21% of 2-exomethyl-2-endo-(4-methyl-3-pentenyl)-3-methylenebicyclo[2.2.1]heptane in methylene chloride (10 mL) and water (1 mL) was reacted with 65% calcium hypochlorite (0.143 g) and solid carbon dioxide (2.0 g), as described in Example 11, to yield 0.462 g (97%) of a mixture of 7-(3-chloro-4-methyl-4-pentenyl)-1,7-dimethyltricyclo[2.2.1.0$^{2,6}$]heptane, 2-endo-methyl-2-exo-(3-chloro-4-methyl-4-pentenyl)-3-methylenebicyclo[2.2.1]heptane, and 2-exo-methyl-2-endo-(3-chloro-4-methyl-4-pentenyl)-3-methylenebicyclo[2.2.1]heptane in about a 4:2:2 ratio (as indicated by NMR analysis). NMR (CDCl$_3$) δ 0.83 (5H, 2s), 1.02 (3H, s), 1.81 (3H, s), 2.7–2.9 (1H, m), 4.20–4.70 (1H, m), 4.46 and 4.75 (2H, 2s), 4.90 and 5.02 (2H, 2 broad s). IR (film) $\nu_{max}$ 2950, 1650, 1450, 1370, 900, 875 cm$^{-1}$.

EXAMPLE 15

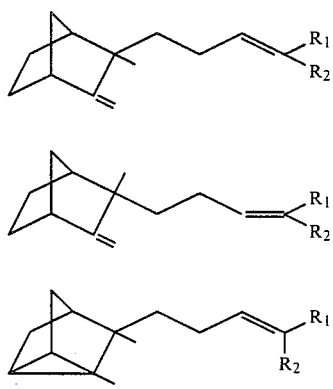

A mixture of santalenyl chlorides (0.462 g, product from Example 14), potassium acetate (0.588 g), potassium iodide (0.066 g) and N,N-dimethylacetamide (4 mL) was heated at 90°–100° C. for 2.5 h. Work-up as described in Example 2 provided 0.464 g (92% yield) of a mixture of santalol acetates. NMR (CDCl$_3$) δ 0.82 (5H, 2s), 0.98 (3H, s), 1.63 and 1.72 (3H, 2 broad s, E/Z isomers, respectively), 2.03 (3H, s), 0.9–2.5 (9H, m), 2.7–2.9 (1H, m), 4.42 and 4.55 (2H, 2s, ratio, 1:3, E/Z isomers, respectively), 4.42 and 4.68 (2H, 2s), 5.1–5.5 (1H, m). IR (film) $\nu_{max}$ 2960, 1735, 1650, 870 cm$^{-1}$. MS (all components have similar mass spectra) (m/e) 202, 187, 161, 94, 43.

EXAMPLE 16

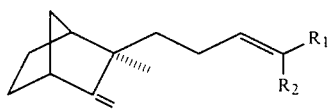

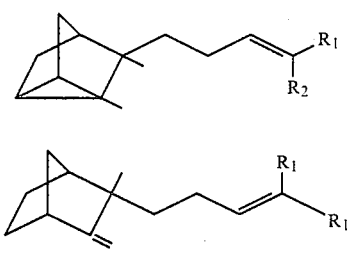

R$_1$, R$_2$=CH$_3$ or CH$_2$OH

The santalol acetates (0.464 g, from Example 15 were stirred with potassium hydroxide (0.4 g) in methanol (20 mL) and water (4 mL) for 40 min. Water was added and the mixture was extracted with hexanes. Evaporation of solvents gave 0.385 g of crude product. Column chromatography, followed by kugelrohr distillation (130° C. 0.3 mm) gave 0.261 g (59% yield from the mixture of santalenes in Example 14) of a colorless oil which GLC analysis showed contained 23% of (Z,E-2-methyl-5-(2-endo-methyl-3-methylenebicyclo[2.2.1]hept-2-yl)-2-penten-1-ol, 21% of (Z,E)-2-methyl-5-(2-exo-methyl-3-methylenebicyclo[2.2.1]hept-2-yl)-2-penten-1-ol and 45% of (Z,E)-2-methyl-5-(1,7-dimethyltricyclo[2.2.1.0$^{2,6}$]-hept-7-yl)-2-penten-1-ol. The Z/E ratio of all the above compounds is 7:3.

EXAMPLE 17

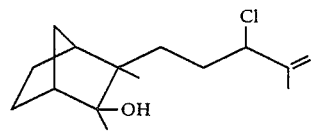

3-(4-Methyl)-3-pentenyl-2,3-endo-dimethylbicyclo[2.2.1]heptan-2-ol (0.147 g, prepared as described in B. J. Willis, P. A. Christenson and D. H. R. Barton, U.S. Pat. No. 4,223,167) in methylene chloride (4 mL) and water (0.4 mL) was reacted with 65% calcium hypochlorite (0.073 g) and solid carbon dioxide (~0.5 g), as described in Example 11, to give 0.164 g (96% yield) of 3-(3-chloro-4-methyl-4-pentenyl)-2,3-endo-dimethylbicyclo[2.2.1]heptan-2-ol. NMR (CDCl$_3$) δ 0.88 (3H, s), 1.18 (3H, s), 1.80 (3H, s), 1.0–2.5 (13H, m), 4.2–4.6 (1H, m), 4.90 and 5.02 (2H, 2 broad s). IR (film) (CDCl$_3$) $\nu_{max}$ 3600, 3375, 2950, 1640, 895 cm$^{-1}$.

EXAMPLE 18

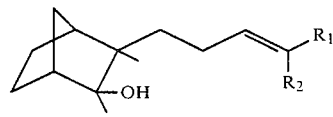

R$_1$, R$_2$=CH$_3$ or CH$_2$OAc

A mixture of 3-(3-chloro-4-methyl-4-pentenyl)-2,3-endodimethylbicyclo[2.2.1]heptan-2-ol (0.164 g), potassium iodide (0.022 g), potassium acetate (0.195 g) and N,N-dimethylacetamide (1.5 mL) was heated at 90°–100° C. for 2 h. Work-up, as described in Example 12, and chromatography gave 0.053 g (29% yield) of (Z,E)-3-(4-methyl-5-acetoxy-3-pentenyl)-2,3-endo-dimethylbicyclo[2.2.1]heptan-2-ol. NMR analysis indicates a Z/E ratio of 5:2. NMR (CDCl$_3$) δ 0.88 (3H, s, broad s, E/Z isomers, respectively), 1.0–2.6 (12H, m), 2.05 (3H, s), 4.43 and 4.60 (2H, 2s, E/Z isomers, ratio, 2:5), 5.2–5.5 (1H, m). IR (CDCl$_3$) $\nu_{max}$ 3600, 3400, 2950, 1730, 1650 cm$^{-1}$. MS (m/e) 220, 205, 202, 187.

As will be apparent to those skilled in the art, in the light of the foregoing disclosure, many alterations, modification, substitutions and combinations are possible in the practice of this invention without departing from the spirit or scope thereof.

What is claimed is:

1. A compound having the structure:

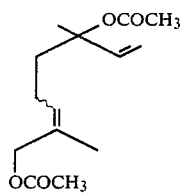

2. A compound having the structure:

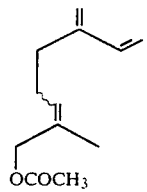

3. A compound having the structure:

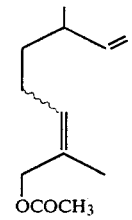

4. A compound having the structure:

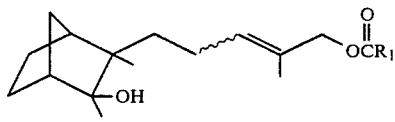

wherein R$_1$ is hydrogen or an alkyl group containing between about 1 and about 4 carbon atoms.

5. The compound of claim 4 wherein R$_1$ is CH$_3$.

* * * * *